(12) United States Patent
Chen et al.

(10) Patent No.: US 12,419,922 B2
(45) Date of Patent: Sep. 23, 2025

(54) STRAIN OF LACTOBACILLUS FERMENTUM CAPABLE OF PREVENTING AND/OR TREATING PERIODONTITIS AND APPLICATION

(71) Applicant: Jiangnan University, Wuxi (CN)

(72) Inventors: Wei Chen, Wuxi (CN); Qiuxiang Zhang, Wuxi (CN); Wanqing Xu, Wuxi (CN); Wenwei Lu, Wuxi (CN); Hao Zhang, Wuxi (CN); Jianxin Zhao, Wuxi (CN)

(73) Assignee: Jiangnan University, Wuxi (CN)

(*) Notice: Subject to any disclaimer, the term of this patent is extended or adjusted under 35 U.S.C. 154(b) by 475 days.

(21) Appl. No.: 18/050,093

(22) Filed: Oct. 27, 2022

(65) Prior Publication Data
US 2023/0082296 A1    Mar. 16, 2023

Related U.S. Application Data

(63) Continuation of application No. PCT/CN2021/121338, filed on Sep. 28, 2021.

(30) Foreign Application Priority Data

Dec. 21, 2020  (CN) .......................... 202011522325.8

(51) Int. Cl.
*A61K 39/02* (2006.01)
*A23G 4/12* (2006.01)
*A61K 35/747* (2015.01)
*A61Q 11/00* (2006.01)

(52) U.S. Cl.
CPC ............ *A61K 35/747* (2013.01); *A23G 4/123* (2013.01); *A61Q 11/00* (2013.01)

(58) Field of Classification Search
None
See application file for complete search history.

(56) References Cited

U.S. PATENT DOCUMENTS

2004/0197277 A1* 10/2004 Gonzales ................. A23G 4/08
424/48

FOREIGN PATENT DOCUMENTS

| CN | 102226157 A | 10/2011 |
| CN | 111642746 A | 9/2020 |
| CN | 111904985 A | 11/2020 |
| CN | 112608864 A | 4/2021 |
| JP | 2012044951 A | 3/2012 |

OTHER PUBLICATIONS

Chen LJ et. al., "In Vitro Antagonistic Growth Effects of Lactobacillus Fermentum and Lactobacillus Salivarius and Their Fermentative Broth on Periodontal Pathogens", Brazilian Journal of Microbiology, V43, No. 4, Dec. 31, 2012, p. 1376-1384.

* cited by examiner

*Primary Examiner* — Jennifer E Graser
(74) *Attorney, Agent, or Firm* — IPro, PLLC; Na Xu (57) ABSTRACT

The present disclosure discloses a strain of *Lactobacillus fermentum* capable of preventing and/or treating periodontitis and an application thereof, belonging to the field of microbiology technology. The present disclosure has screened to obtain a strain of *L. fermentum* CCFM1139. The *L. fermentum* CCFM1139 can alleviate periodontitis by inhibiting formation of mixed bacterial biofilms of *Porphyromonas gingivalis*, *Prevotella intermedia* and *Fusobacterium nucleatum*, thereby reducing the amount of biofilm by 52.45%, and can reduce the content of TNF-α from 131.37 pg/mL to 83.31 pg/mL and IL-8 from 147.70 pg/mL to 121.12 pg/mL in a periodontitis cell model, reduce colonization of the *P. gingivalis* and the *F. nucleatum* in the oral cavity by 1-2 orders of magnitude, and reduce the amount of the alveolar bone resorption from 1838.0 μm to 805.7 μm.

6 Claims, 8 Drawing Sheets
Specification includes a Sequence Listing.

SEQUENCE LISTING

```
Sequence total quantity: 1
SEQ ID NO: 1            moltype = DNA  length = 1378
FEATURE                 Location/Qualifiers
source                  1..1378
                        mol_type = other DNA
                        organism = Lactobacillus fermentum
SEQUENCE: 1
gcggtgtgta caaggcccgg gaacgtattc accgcgccat gctgatccgc gattactagc   60
gattccgact tcgtgcaggc gagttgcagc ctgcagtccg aactgagaac ggttttaaga  120
gatttgcttg ccctcgcgag ttcgcgactc gttgtaccgt ccattgtagc acgtgtgtag  180
cccaggtcat aaggggcatg atgatctgac gtcgtcccca ccttcctccg gtttgtcacc  240
ggcagtctca ctagagtgcc caacttaatg ctggcaacta gtaacaaggg ttgcgctcgt  300
tgcgggactt aacccaacat ctcacgacac cgaccatgca ccacctgtca               360
ttgcgttccc gaaggaaacg ccctatctct agggttggcg caagatgtca agacctggta  420
aggttcttcg cgtagcttcg aattaaacca catgctccac cgcttgtgcg ggcccccgtc  480
aattcctttg agtttcaacc ttgcggtcgt actccccagg cggagtgctt aatgcgttag  540
ctccggcact gaagggcgga aaccctccaa cacctagcac tcatcgttta cggcatggac  600
taccagggta tctaatcctg ttcgctaccc atgctttcga gtctcagcgt cagttgcaga  660
ccaggtagcc gccttcgcca ctggtgttct tccatatatc tacgcattcc accgctacac  720
atggagttcc actaccctct tctgcactca agttatccga tttccgatgc acttctccgg  780
ttaagccgaa ggctttcaca tcagacttag aaaaccgcct gcactctctt tacgcccaat  840
aaatccggat aacgcttgcc acctacgtat taccgcggct gctggcacgt agttagccgt  900
gactttctgg ttaaataccg tcaacgtatg aacagttact ctcatacgtg ttcttcttta  960
acaacagagc tttacgagcc gaaaccsttc ttcactcacg cggtgttgct ccatcaggct 1020
tgcgcccatt gtggaagatt ccctactgct gcctcccgta ggagtatggg ccgtgtctca 1080
gtccattgt ggccgatcag tctctcaact cggctatgca tcatcgcctt ggtaggccgt 1140
taccccacca acaagctaat gcaccgcagg tccatccaga agtgatagcg agaagccatc 1200
ttttaagcgt tgttcatgcg aacaacgttg ttatgcggta ttagcatctg tttccaaatg 1260
ttgtcccccg cttctgggca ggttacctac gtgttactca cccgtccgcc actcgttggc 1320
gaccaagatc aatcaggtgc aagcaccatc aatcaattgg gccaacgcgt tcgactgc   1378
```

STRAIN OF LACTOBACILLUS FERMENTUM CAPABLE OF PREVENTING AND/OR TREATING PERIODONTITIS AND APPLICATION

The instant application contains a Sequence Listing in XML format as a file named "YGHY-2022-24-SEQ.xml", created on Aug. 31, 2022, of 4 kB in size, and which is hereby incorporated by reference in its entirety.

TECHNICAL FIELD

The present disclosure relates to a strain of *Lactobacillus fermentum* capable of preventing and/or treating periodontitis and application, belonging to the field of microbiology technology.

BACKGROUND

Periodontitis is a common oral disease causing loss of periodontal tissue attachment and eventually leading to loosening and loss of teeth. The main pathogens of periodontitis include Gram-negative anaerobic bacteria such as *Porphyromonas gingivalis, Fusobacterium nucleatum* and *Prevotella intermedia*. Infections caused by microorganisms do not only lead to destruction of gingival and periodontal tissues, but also stimulate body's immune response, causing the host to continuously release various inflammatory factors, thereby leaving the body in a state of chronic inflammation.

Under normal conditions, there is a balance between various microorganisms in subgingival areas and an environment rich in immune inflammatory mediators, allowing to achieve homeostasis in the host periodontal tissue. While once the balance is disrupted, pathogenic bacteria originally behaving in a symbiotic state will exhibit pathogenicity in a dysregulated state. The pathogens and host release large amounts of proteolytic enzymes capable of destroying periodontal tissues, thus stimulating neutrophils to release a variety of enzymes to break down periodontal supporting and connective tissues. By releasing virulence factors such as lipopolysaccharide into the gingival sulcus, plaque bacteria stimulate the release of inflammatory mediators from immune cells and osteoblasts in the tissue, activate macrophages and fibroblasts to secrete cytokines, and induce massive osteoclast formation and alveolar bone resorption.

Cytokines such as IL-8 and TNF-α also play an important role in the progression of periodontitis and bone resorption. Most of these cytokines are produced by macrophages, epithelial cells, fibroblasts or the like in response to microorganisms, bacterial toxins or body injuries. These cytokines can induce proliferation and differentiation of osteoclast precursor cells and indirectly act on mature osteoclasts to stimulate bone resorption while inhibiting bone formation. Many studies have shown that gingival tissues of patients with periodontitis have high levels of cytokines such as TNF-α and IL-8.

Discovering non-antibiotic, safe and effective treatment methods is a major research hotspot at present. *Lactobacillus*, as a class of probiotics, is gradually being applied to the intervention and treatment of oral diseases with advantages of being economical and little toxic and side effects.

SUMMARY

The present disclosure provides a strain of *L. fermentum* CCFM1139, and the *L. fermentum* CCFM1139 is taxonomically named *Lactobacillus fermentum* and was deposited in the Guangdong Microbial Culture Collection Center on Aug. 1, 2020, with the deposit number of GDMCC No: 61116, at the $5^{th}$ floor of Building 59, Compound 100, Xianlie Middle Road, Guangzhou.

The *L. fermentum* CCFM1139 is from Yangzhou area, the strain was sequenced and analyzed, and its 16S rDNA sequence is shown in SEQ ID NO.1. The sequence obtained by sequencing was aligned in NCBI for nucleic acid sequences. The result shows that the strain is *L. fermentum* with 99.85% homology, and is named as *Lactobacillus fermentum* CCFM1139.

*L. fermentum* CCFM1139 colonies on an MRS medium are small, translucent, white and round.

The present disclosure also provides a product for preventing and/or treating periodontitis, and the product contains the above *L. fermentum* CCFM1139.

In one embodiment of the present disclosure, in the product, the viable count of the *L. fermentum* CCFM1139 is not less than $1\times10^9$ CFU/mL or $1\times10^{12}$ CFU/g.

In one embodiment of the present disclosure, the product is a drug, food or daily chemical product.

In one embodiment of the present disclosure, the composition of the drug includes the above *L. fermentum* CCFM1139 and a drug carrier.

In one embodiment of the present disclosure, the carrier is a pharmaceutically acceptable carrier.

In one embodiment of the present disclosure, the carrier is one or more of a pharmaceutically acceptable filler, wetting agent, disintegrating agent, binder, lubricant or corrigent.

In one embodiment of the present disclosure, the food is a yogurt or chewing gum of the above *L. fermentum* CCFM1139.

In one embodiment of the present disclosure, the daily chemical product is a mouthwash or toothpaste containing the above *L. fermentum* CCFM1139.

The present disclosure also provides a method for preparing a product for preventing and/or treating periodontitis, and the method is that the above *L. fermentum* CCFM1139 is used in preparation of the product.

In one embodiment of the present disclosure, in the product, the viable count of the above *L. fermentum* CCFM1139 is not less than $1\times10^9$ CFU/mL or $1\times10^{12}$ CFU/g.

In one embodiment of the present disclosure, the product is a drug, food or daily chemical product.

In one embodiment of the present disclosure, the composition of the drug includes the above *L. fermentum* CCFM1139 and a carrier.

In one embodiment of the present disclosure, the carrier is a pharmaceutically acceptable carrier.

In one embodiment of the present disclosure, the carrier is one or more of a pharmaceutically acceptable filler, wetting agent, disintegrating agent, binder, lubricant and corrigent.

In one embodiment of the present disclosure, the food is a yogurt or chewing gum containing the above *L. fermentum* CCFM1139.

In one embodiment of the present disclosure, the daily chemical product is a mouthwash or toothpaste containing the above *L. fermentum* CCFM1139.

The present disclosure also provides an application of the above *L. fermentum* CCFM1139 in preparation of a food, drug or cosmetics inhibiting the *P. intermedia*, the *P. gingivalis* and/or the *F. nucleatum*.

Beneficial Effects

1. The present disclosure screened to obtain a strain of *L. fermentum* CCFM1139, and the *L. fermentum* CCFM1139 has the effect of relieving periodontitis, specifically reflected in the followings:
    (1) It can inhibit formation of mixed bacterial biofilms of the *P. gingivalis*, the *P. intermedia* and the *F. nucleatum*, thereby reducing the amount of biofilm by 52.45%.
    (2) It can reduce the content of TNF-α in a periodontitis cell model from 131.37 pg/mL to 83.31 pg/mL by 37%, and reduce the content of IL-8 in a periodontitis cell model from 147.70 pg/mL to 121.12 pg/mL by 18%.
    (3) It can increase expression of Occludin in a periodontitis cell model from 0.42 to 0.67 by 60%, and increase expression of Claudin-1 from 0.55 to 0.69 by 25%.
    (4) It can increase the body weight of rats with periodontitis from 245.20 g to 322.58 g, basically close to the blank group.
    (5) It can reduce colonization of the *P. gingivalis* and the *F. nucleatum* in the oral cavity of rats by 1-2 orders of magnitude.
    (6) It can reduce the amount of the alveolar bone resorption of rats with periodontitis from 1838.0 μm to 805.7 μm.

Therefore, this *L. fermentum* CCFM1139 has great application prospects in preparation of products (such as a drug, food or daily chemical product) for preventing and/or treating periodontitis.

2. The *L. fermentum* is a kind of probiotics, and has been included in the List of Bacteria that Can Be Used in Food issued by the Ministry of Health. Therefore, the *L. fermentum* CCFM1139 obtained from the present disclosure through screening does not bring any side effects to a human body, and is relatively safe when used in products (such as a drug, food or daily chemical product) for preventing and/or treating periodontitis.

Biomaterial Deposit

A strain of *L. fermentum* CCFM1139, is taxonomically named *Lactobacillus fermentum* and was deposited in the Guangdong Microbial Culture Collection Center on Aug. 1, 2020, with the deposit number of GDMCC No: 61116, at the 5$^{th}$ floor of Building 59, Compound 100, Xianlie Middle Road, Guangzhou.

DETAILED DESCRIPTION

The present disclosure is further described below in conjunction with specific examples and the accompanying drawings.

The *P. gingivalis* involved in the following examples was purchased from the Guangdong Microbial Culture Collection Center, with product No. GDMCC 1.851; the *F. nucleatum* involved in the following examples was purchased from the Guangdong Microbial Culture Collection Center, with product No. GDMCC 1.1290; the *P. intermedia* involved in the following examples was purchased from the Guangdong Microbial Culture Collection Center, with product No. GDMCC 1.849; the oral epithelial cancer cells Ca9-22 involved in the following examples was purchased from BeNa Culture Collection Co., Ltd.; *P. gingivalis* lipopolysaccharide involved in the following examples was purchased from InvivoGen, France; the lysozyme involved in the following examples was purchased from Sangon Biotech (Shanghai) Co., Ltd.; DMEM medium and fetal bovine serum in the following examples were purchased from Gibco, USA; and SPF-grade Wistar rats involved in the following examples were purchased from Beijing Vital River Laboratory Animal Technology Co., Ltd. (Production License No. SCXK (Beijing) 2012-0001).

Culture Media Involved in the Following Examples are as Follows

MRS medium: yeast powder 5.0 g/L, beef extract 10.0 g/L, peptone 10.0 g/L, glucose 20.0 g/L, anhydrous sodium acetate 2.0 g/L, diammonium hydrogen citrate 2.0 g/L, dipotassium hydrogen phosphate trihydrate 2.6 g/L, manganese sulfate monohydrate 0.25 g/L, magnesium sulfate heptahydrate 0.5 g/L, and Tween-80 1 mL/L, pH 6.2-6.4.

BHI medium: tryptone 10.0 g/L, bovine heart extract 17.5 g/L, sodium chloride 5.0 g/L, yeast extract 5.0 g/L, glucose 2.0 g/L, disodium hydrogen phosphate dodecahydrate 2.5 g/L, L-cysteine hydrochloride monohydrate 0.4 g/L, and 0.5% vitamin K1-hemoglobin chloride 1 mL/L, pH 7.2-7.4.

Bacterial Suspensions Involved in the Following Examples were Prepared as Follows

*F. nucleatum* suspension: The *F. nucleatum* was inoculated into a BHI medium at an inoculum volume of 2% (v/v) of the total volume of the BHI medium and incubated anaerobically at 37° C. for 48 h, and then the concentration of the bacteria was adjusted to $1 \times 10^9$ CFU/mL with the BHI medium.

*P. gingivalis* suspension: The *P. gingivalis* was inoculated into a BHI medium at an inoculum volume of 2% (v/v) of the total volume of the BHI medium and incubated anaerobically at 37° C. for 48 h, and then the concentration of the bacteria was adjusted to 1×10$^9$ CFU/mL with the BHI medium.

*P. intermedia* suspension: The *P. intermedia* was inoculated into a BHI medium at an inoculum volume of 2% (v/v) of the total volume of the BHI medium and incubated anaerobically at 37° C. for 48 h, and then the concentration of the bacteria was adjusted to 1×10$^9$ CFU/mL with the BHI medium.

A PBS Buffer Involved in the Following Examples was Prepared as Follows

PBS buffer: sodium chloride 8 g/L, disodium hydrogen phosphate dodecahydrate 3.63 g/L, potassium dihydrogen phosphate 0.24 g/L, and potassium chloride 0.2 g/L, pH 7.4.

Example 1: Screening and Strain Identification of *L. fermentum* CCFM1139

1. Screening

Feces samples were from healthy people in Yangzhou area. The samples were pretreated and preserved in 20% glycerol in a −80° C. refrigerator. After being taken out and thawed, the samples were mixed uniformly, and 0.5 mL of the samples were pipetted and added to 4.5 mL of 9 g/L saline for gradient dilution. Appropriate gradient dilutions were selected and applied to an MRS medium containing 20 g/L of agar, and incubated at 37° C. for 48 h. Typical colonies of the *L. fermentum* were picked and streaked on an MRS medium containing 20 g/L of agar for purification. Single colonies were picked and transferred to an MRS medium for multiplication, and deposited in 30% glycerol to obtain strain CCFM1139 and strains 1-19 screened at the same time, respectively. The typical colonies of the *L. fermentum* were small, translucent, white and round.

2. Identification

Genomes of the strain CCFM1139 and strains 1-19 were extracted separately, 16S rDNA of the strain CCFM1139 and strains 1-19 were amplified and sequenced (conducted by Invitrogen, nucleotide sequences of the 16S rDNA obtained from CCFM1139 amplification are shown in SEQ ID NO.1), and the sequences were aligned in NCBI for nucleic acid sequences. The results showed that both the strain CCFM1139 and strains 1-19 were the *L. fermentum*, and named *Lactobacillus fermentum* CCFM1139 (original strain number 96) and *Lactobacillus fermentum* 1-19, respectively.

Example 2: Effect of *L. fermentum* CCFM1139 on Amount of Mixed Bacterial Biofilms The experiment was divided into two groups, a *L. fermentum*-mediated group and a blank control group.

The *L. fermentum*-mediated group was treated according to the following methods:
(1) Single colonies of stains of the *L. fermentum* CCFM1139 and *L. fermentum* 1-19 were inoculated into an MRS medium and incubated at 37° C. for 12 h to prepare and obtain a seed solution. The obtained seed solution was inoculated into an MRS medium at an inoculum volume of 2% of the total volume of the MRS medium and incubated at 37° C. for 24 h to obtain a culture solution. The culture solution was centrifuged at 8000 r/min and 4° C. for 5 min to obtain a supernatant. The supernatant was filtered through a 0.22 μm sterile filter membrane to obtain supernatants of the *L. fermentum* CCFM1139 and *L. fermentum* 1-19 both with a bacterial concentration of 1×10$^9$ CFU/mL respectively.

(2) 40 μL of each of *P. intermedia*, *P. gingivalis* and *F. nucleatum* suspensions was added to a 96-well plate to obtain mixed bacterial suspensions, then 80 μL of each of the supernatants of the *L. fermentum* CCFM1139 and *L. fermentum* 1-19 obtained from step (1) was added respectively, and the mixture was incubated anaerobically at 37° C. for 48 h to obtain mixed bacterial biofilms.

(3) The mixed bacterial biofilms obtained in the 96-well plate were washed 2 times with a PBS buffer and stood to dry at 25° C. 100 μL of crystalline violet solution with a concentration of 0.1% (v/v) was added to the 96-well plate to stain the mixed bacterial biofilms for 30 min. The stained mixed bacterial biofilms were washed 2 times with a PBS buffer. 100 μL of ethanol with a concentration of 95% (v/v) was added to the 96-well plate for dissolution. An absorbance value at $OD_{600}$ was read in an enzyme-labeled instrument to obtain the amount of mediated mixed bacterial biofilms. The reduction of the mixed bacterial biofilms after being mediated by the *L. fermentum* CCFM1139 and *L. fermentum* 1-19 was calculated by the amount of the mediated mixed bacterial biofilms.

The blank control group: on the basis of the *L. fermentum*-mediated group, a supernatant of the *L. fermentum* CCFM1139 was replaced with a blank MRS medium to obtain the amount of mixed bacterial biofilms in the blank control group.

Reduction of mediated mixed bacterial biofilms (%)= (amount of mixed bacterial biofilms in blank control group−amount of mediated mixed bacterial biofilms)/amount of mixed bacterial biofilms in blank control group.

The calculated results are shown in Table 1: the absorbance of mixed bacterial biofilms formed by the *P. intermedia*, *P. gingivalis* and *F. nucleatum* was 3.639. The reduction of the mixed bacterial biofilms by 20 strains of *L. fermentum* ranged from 1% to 53%. The *L. fermentum* CCFM1139 had the best inhibition effect, the absorbance was 1.730 after mediation by the *L. fermentum* CCFM1139, and the amount of the mixed bacterial biofilms was reduced by 52.45%, with the best effect in the 20 strains of *L. fermentum*.

It can be seen that the *L. fermentum* CCFM1139 can effectively inhibit the mixed bacterial biofilms formed by the *P. intermedia*, *P. gingivalis* and *F. nucleatum* and effectively alleviate the formation of periodontitis.

TABLE 1

Reduction of mixed bacterial biofilms after mediation by different *L. fermentum*

| Group | Absorbance | Reduction of biofilm |
|---|---|---|
| Blank control group | 3.639 ± 0.158 | 0.00% |
| *L. fermentum* CCFM1139 | 1.730 ± 0.049 | 52.45% |
| *L. fermentum* 1 | 2.499 ± 0.035 | 31.34% |
| *L. fermentum* 2 | 3.036 ± 0.181 | 16.57% |
| *L. fermentum* 3 | 3.300 ± 0.025 | 9.32% |
| *L. fermentum* 4 | 1.793 ± 0.047 | 50.73% |
| *L. fermentum* 5 | 2.657 ± 0.198 | 27.00% |
| *L. fermentum* 6 | 3.551 ± 0.078 | 2.42% |
| *L. fermentum* 7 | 2.176 ± 0.051 | 40.20% |
| *L. fermentum* 8 | 3.462 ± 0.046 | 4.85% |
| *L. fermentum* 9 | 2.103 ± 0.053 | 43.02% |
| *L. fermentum* 10 | 1.833 ± 0.008 | 49.64% |

TABLE 1-continued

Reduction of mixed bacterial biofilms after mediation by different
L. fermentum

| Group | Absorbance | Reduction of biofilm |
|---|---|---|
| L. fermentum 11 | 3.327 ± 0.058 | 8.56% |
| L. fermentum 12 | 3.203 ± 0.028 | 12.00% |
| L. fermentum 13 | 2.103 ± 0.053 | 42.22% |
| L. fermentum 14 | 3.542 ± 0.098 | 2.67% |
| L. fermentum 15 | 3.578 ± 0.037 | 1.67% |
| L. fermentum 16 | 3.478 ± 0.065 | 4.42% |
| L. fermentum 17 | 2.738 ± 0.185 | 24.76% |
| L. fermentum 18 | 2.155 ± 0.080 | 40.79% |
| L. fermentum 19 | 3.142 ± 0.086 | 13.67% |

Example 3: Effect of L. fermentum CCFM1139 on Content of TNF-α and IL-8 in a Periodontitis Cell Model Periodontitis cell model construction: oral epithelial cancer cells Ca9-22 were inoculated into a DMEM medium containing 10% (v/v) fetal bovine serum and activated by incubation in a cell culture incubator at 37° C. with a gas phase containing 5% (v/v) $CO_2$ until the cell concentration was $2\times10^5$ cells/mL. A Ca9-22 cell culture solution was added to a 6-well plate with 2 mL per well. The 6-well plate was preincubated at 37° C. for 2 h. 1 μg/mL of the P. gingivalis lipopolysaccharide was added to each well.

The experiment was divided into three groups: a L. fermentum-mediated group, a negative control group and a blank control group.

The L. fermentum-mediated group was treated according to the following methods:
(1) Single colonies of stains of the L. fermentum CCFM1139 and L. fermentum 1-8 were inoculated into an MRS medium and incubated at 37° C. for 12 h, respectively, to prepare and obtain a seed solution. The obtained seed solution was inoculated into an MRS medium at an inoculum volume of 2% of the total volume of the MRS medium, respectively, and incubated at 37° C. for 24 h to obtain a culture solution, respectively. The culture solution was centrifuged at 8000 r/min and 4° C. for 5 min to obtain a supernatant. The supernatant was filtered through a 0.22 μm sterile filter membrane to obtain supernatants of the L. fermentum CCFM1139 and L. fermentum 1-8 both with a bacterial concentration of $10^9$ CFU/mL respectively.
(2) The supernatants of the L. fermentum CCFM1139 and L. fermentum 1-8 obtained in step (1) were added to a periodontitis cell model at an inoculum volume of 3% (v/v), respectively, and incubated at 37° C. for 4 h. The cell supernatants were collected from the 6-well plate and centrifuged at 3000 r/min and 4° C. for 20 min. The content of TNF-α and IL-8 in the cell supernatants was determined with an ELISA kit.

The negative control group (CELL+LPS group): 3% (v/v) of an MRS medium was added to a periodontitis cell model.

The blank control group (CELL group): on the basis of the L. fermentum-mediated group, the P. gingivalis lipopolysaccharide and 3% (v/v) of a supernatant of the L. fermentum CCFM1139 or the L. fermentum 1-8 were not added to a 6-well plate.

Figure 1:
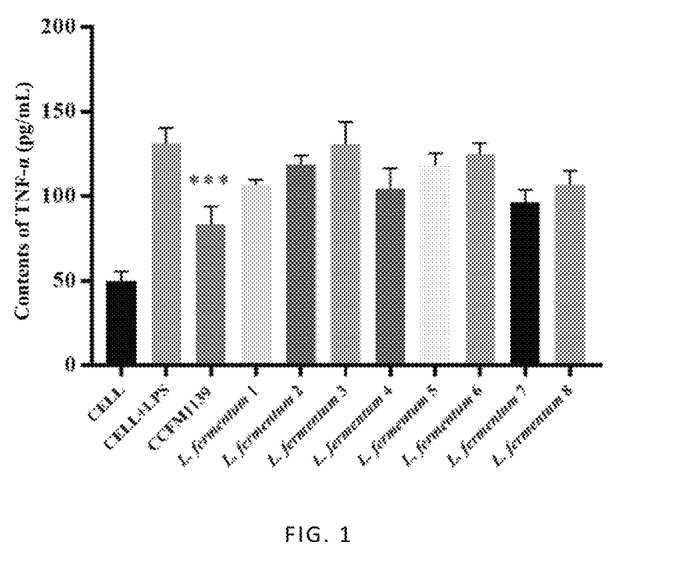
FIG. 1 shows the content of TNF-α in different groups of periodontitis cell models.
Figure 2:
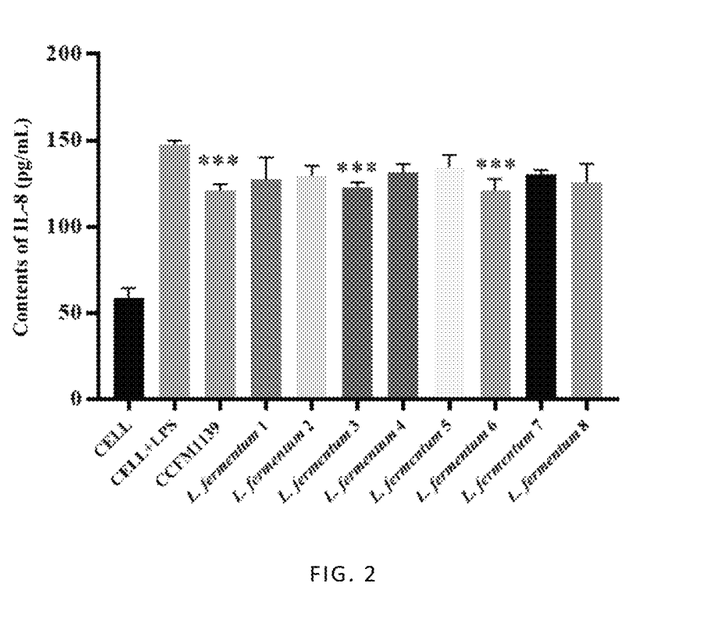
FIG. 2 shows the content of IL-8 in different groups of periodontitis cell models.

The results are shown in FIGS. 1-2: compared with the blank control group (CELL group), the negative control group (CELL+LPS group) showed an increase in expression of TNF-α from 49.69 pg/mL (blank control group) to 131.37 pg/mL (negative control group) under the stimulation of the P. gingivalis lipopolysaccharide.

As shown in FIG. 1, expression of TNF-α after mediation by the L. fermentum CCFM1139 reduced from 131.37 pg/mL (negative control group) to 83.31 pg/mL (CCFM1139 group) by 37%, and had a highly significant difference (p<0.001) compared with the negative control group (CELL+LPS group). While the group after mediation by other L. fermentum did not have the effect of reducing expression of TNF-α or was less effective than the L. fermentum CCFM1139.

As shown in FIG. 2, compared with the blank control group (CELL group), expression of IL-8 in the negative control group (CELL+LPS group) increased from 58.78 pg/mL (blank control group) to 147.70 pg/mL (negative control group) under the stimulation of the P. gingivalis lipopolysaccharide.

L. fermentum 3 and 6 and CCFM1139 all significantly reduced expression of IL-8 (p<0.001), with the L. fermentum CCFM1139 having the best effect and reducing expression of IL-8 from 147.70 pg/mL to 121.12 pg/mL by 18%.

Example 4: Effect of L. fermentum CCFM1139 on Expression of Occludin and Claudin-1 in a Periodontitis Cell Model Periodontitis cell model construction: oral epithelial cancer cells Ca9-22 were inoculated into a DMEM medium containing 10% (v/v) fetal bovine serum and activated by incubation in a cell culture incubator at 37° C. with a gas phase containing 5% (v/v) $CO_2$ until the cell concentration was $2\times10^5$ cells/mL. A Ca9-22 cell culture solution was added to a 6-well plate with 2 mL per well. The 6-well plate was preincubated at 37° C. for 2 h. 1 μg/mL of the P. gingivalis lipopolysaccharide was added to each well.

The experiment was divided into three groups: a L. fermentum-mediated group, a negative control group (CELL+LPS group) and a blank control group (CELL group).

The L. fermentum-mediated group was treated according to the following methods:
(1) Single colonies of stains of the L. fermentum CCFM1139 and L. fermentum 1-3 were inoculated into an MRS medium and incubated at 37° C. for 12 h, respectively, to prepare and obtain a seed solution. The obtained seed solution was inoculated into an MRS medium at an inoculum volume of 2% of the total volume of the MRS medium, respectively, and incubated at 37° C. for 24 h to obtain a culture solution, respectively. The culture solution was centrifuged at 8000 r/min and 4° C. for 5 min to obtain a supernatant. The supernatant was filtered through a 0.22 μm sterile filter membrane to obtain supernatants of the L. fermentum CCFM1139 and L. fermentum 1-3 both with a bacterial concentration of $10^9$ CFU/mL respectively.
(2) The supernatants of the L. fermentum CCFM1139 and L. fermentum 1-3 obtained in step (1) were added to a periodontitis cell model at an inoculum volume of 3% (v/v), respectively, and incubated at 37° C. for 12 h. Total cell RNA was extracted from the incubated 6-well plate by the Trizol method, and reversely transcribed into cDNA according to the instructions of a reverse transcription kit, and fluorescent quantitative PCR is adopted to detect expression of Occludin and Claudin-1 in the cells.

The negative control group (CELL+LPS group): 3% (v/v) of an MRS medium was added to a periodontitis cell model.

The blank control group (CELL group): on the basis of the *L. fermentum*-mediated group, the *P. gingivalis* lipopolysaccharide and 3% (v/v) of a supernatant of the *L. fermentum* CCFM1139 or the *L. fermentum* 1-3 were not added to a 6-well plate.

As shown by the assay results (FIGS. 3-4), the expression of Occludin and Claudin-1 was significantly downregulated in the negative control group (CELL+LPS group) periodontitis cell model compared with the blank control group (CELL group).

Figure 3:
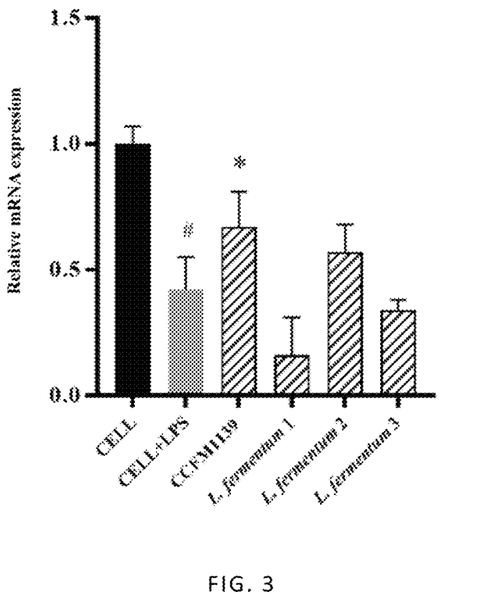
FIG. 3 shows relative expression of Occludin in different groups of periodontitis cell models.
Figure 4:
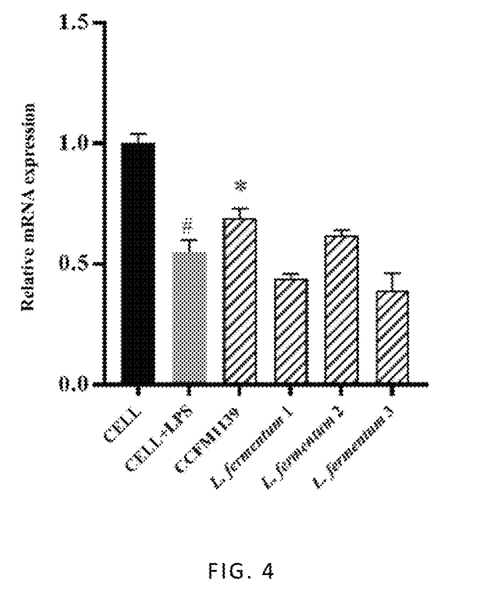
FIG. 4 shows relative expression of Claudin-1 in different groups of periodontitis cell models.

Compared with the *L. fermentum* 1-3, the *L. fermentum* CCFM1139 significantly upregulated expression of Occludin and Claudin-1. As shown in FIG. 3, expression of Occludin in the periodontitis cell model increased from 0.42 (negative control group) to 0.67 (CCFM1139 group) by 60%. As shown in FIG. 4, expression of Claudin-1 in the periodontitis cell model increased from 0.55 (negative control group) to 0.69 (CCFM1139 group) by 25%.

It can be seen that the *L. fermentum* CCFM1139 has a good protective effect on the oral epithelial barrier.

Example 5: Tolerance of *L. fermentum* CCFM1139 to Lysozyme

The specific steps were as follows:

The experiment was divided into two groups, an experimental group and a blank control group.

The experimental group was treated as follows: 200 µL of an MRS medium was added to a 96-well culture plate, and different concentrations of lysozyme solution were added to the 96-well culture plate to make final concentrations of lysozyme in the MRS medium 0.4 mg/mL, 0.8 mg/mL, 1.2 mg/mL, 1.6 mg/mL, 2.0 mg/mL, and 3.0 mg/mL, respectively, to obtain experimental group media 1 to 6, respectively.

The blank control group was treated as follows: 200 µL of an MRS medium was added to a 96-well culture plate and continuing, and sterile water was added to the 96-well culture plate with an equal volume of a lysozyme solution to obtain a blank group medium.

Single colonies of the *L. fermentum* CCFM1139 were inoculated into an MRS medium and incubated at 37° C. for 12 h, respectively, to prepare and obtain a seed solution. The obtained seed solution was inoculated into 96-well culture plates of the experimental group medium 1-6 and the blank group medium at an inoculum volume of 5% of the total volume of the MRS medium to obtain experimental groups 1-6 and a blank control group, respectively, and incubated at 37° C. for 24 h, respectively. After 24 h of incubation, the absorbance of the culture solution in the 96-well culture plates was measured at $OD_{600}$. Tolerance of the *L. fermentum* CCFM1139 to lysozyme was determined according to the absorbance value, and the assay results were shown in FIG. 5.

Figure 5:
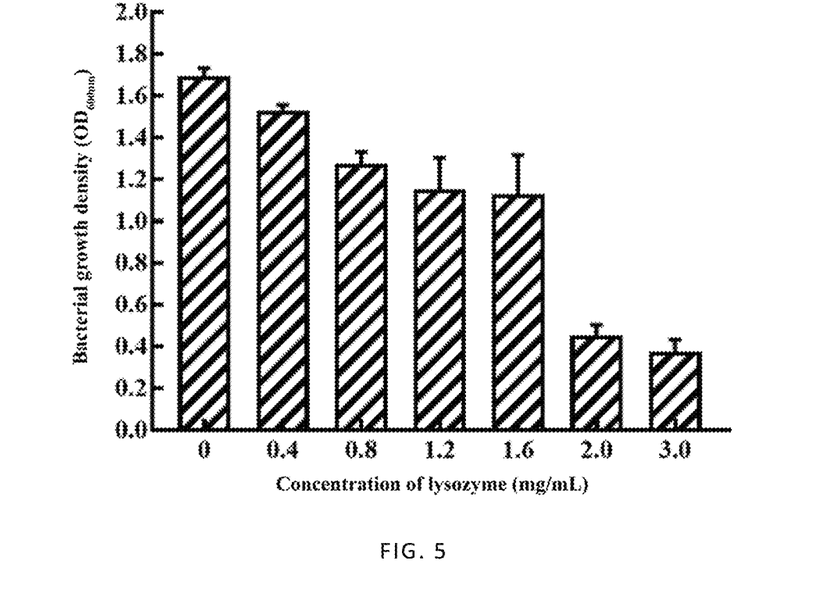
FIG. 5 shows tolerance of the *L. fermentum* CCFM1139 to lysozyme.

According to FIG. 5, tolerance threshold values of the *L. fermentum* CCFM1139 to lysozyme ranged from 1.6 mg/mL to 2.0 mg/mL, much higher than the concentration of lysozyme in human oral saliva (1-57 µg/mL), indicating that, the *L. fermentum* CCFM1139 possesses the ability to survive in the oral environment.

Example 6: Prevention and Treatment of *L. fermentum* CCFM1139 in a Model of Rats with Periodontitis I. Experimental Design Scheme for Rats with Periodontitis 30 male, 5-week-old, SPF-grade Wistar rats weighing 150-170 g were selected and randomly divided into 5 groups with 6 rats each according to the principle of consistent average body weight in each group. The 5 groups were a blank group (Control group), a model group (Model group), a *L. fermentum* CCFM1139 group (CCFM1139 group), a *L. fermentum* 1 group (*L. fermentum* 1 group), and a *L. fermentum* 2 group (*L. fermentum* 2 group).

The experiment was conducted for 5 weeks (beginning of week 0-end of week 4) for a total of 35 days. Except for the blank group, the rats in the other groups underwent periodontitis modeling at the beginning of week 0 of the experiment. The modelling method is: the rats were anesthetized by intramuscular injection of 200 mg/kg of ketamine hydrochloride, and the left maxillary second molars of the rats were ligated with a 0.22 mm orthodontic wire. After the ligation procedure, each rat was given 20 mg of ampicillin orally once every 2 days for 3 times, and then the administration of ampicillin was stopped.

Infestation with the *P. gingivalis*, and *F. nucleatum* suspensions was started in week 1 and continued once every 2 days for 3 times. The infestation was performed by pipetting 1 mL each of the *P. gingivalis*, and *F. nucleatum* suspensions with a sterile syringe, and then tube feeding and fasting for half an hour.

During the experiment, the Model group, the CCFM1139 group, the *L. fermentum* 1 group, and the *L. fermentum* 2 group were fed a feed Keyes 2000 supplemented with distilled water with 10% (m/m) sucrose, and the blank control group was fed a normal diet. The rat groups and diets are shown in Table 2.

TABLE 2

| Grouping of rats | | |
|---|---|---|
| Group | Number | Diet |
| Control group | 6 | Normal diet and water intake |
| Model group | 6 | Feed Keyes 2000, drink 10% sucrose solution |
| CCFM1139 group | 6 | Feed Keyes 2000, drink 10% sucrose solution |
| *L. fermentum* 1 group | 6 | Feed Keyes 2000, drink 10% sucrose solution |
| *L. fermentum* 2 group | 6 | Feed Keyes 2000, drink 10% sucrose solution |

Feed Keyes 2000 (w/w): milk powder 28%, sucrose 56%, wheat flour 6%, yeast 4%, alfalfa flour 3%, liver meal 1%, and salt 2%.

The CCFM1139, *L. fermentum* 1 and *L. fermentum* 2 groups were prevented and treated at the same time by tube feeding of the *P. gingivalis* and *F. nucleatum* suspensions, and water and food fasting for half an hour at the beginning of week 1, followed by tube feeding of *L. fermentum* CCFM1139 suspension, *L. fermentum* 1 suspension or *L. fermentum* 2 suspension, respectively, and water and food fasting for half an hour.

Figure 6:
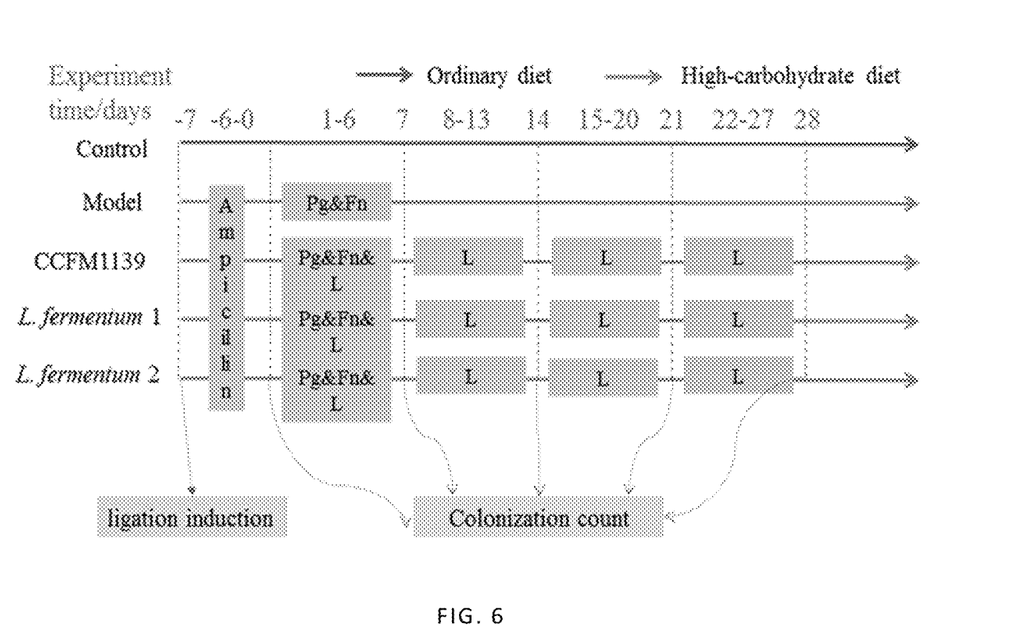
FIG. 6 shows flow chart of the experiment.

After week 1 of modeling, the CCFM1139 group, the *L. fermentum* 1 group and the *L. fermentum* 2 group were continuously prevented and treated with the *L. fermentum* CCFM1139 suspension, the *L. fermentum* 1 suspension or the *L. fermentum* 2 suspension for 3 weeks, respectively. The prevention and treatment were carried out by pipetting 1 mL of *L. fermentum* with a sterile syringe, and tube feeding and water and food fasting for half an hour. The experimental procedure is shown in FIG. 6.

The *L. fermentum* CCFM1139, *L. fermentum* 1 and *L. fermentum* 2 suspensions were prepared as follows:

The *L. fermentum* CCFM1139 suspension: the *L. fermentum* CCFM1139 was inoculated into an MRS medium at an inoculum volume of 2% (v/v) of the total volume of the MRS medium and incubated anaerobically at 37° C. for 24 h. The concentration of the bacteria was adjusted to a final concentration of $1 \times 10^9$ CFU/mL.

The *L. fermentum* 1 suspension: the *L. fermentum* 1 was inoculated into an MRS medium at 2% (v/v) of the total volume of the MRS medium and incubated anaerobically at 37° C. for 24 h. The concentration of the bacteria was adjusted to a final concentration of $1 \times 10^9$ CFU/mL.

The *L. fermentum* 2 suspension: the *L. fermentum* 2 was inoculated into an MRS medium at 2% (v/v) of the total volume of the MRS medium and incubated anaerobically at 37° C. for 24 h. The concentration of the bacteria was adjusted to a final concentration of $1 \times 10^9$ CFU/mL.

II. Experimental results:

1. Effect of *L. fermentum* CCFM1139 on the Body Weight of Rats

The rats were weighed every week and the growth of each rat was compared.

Figure 7:
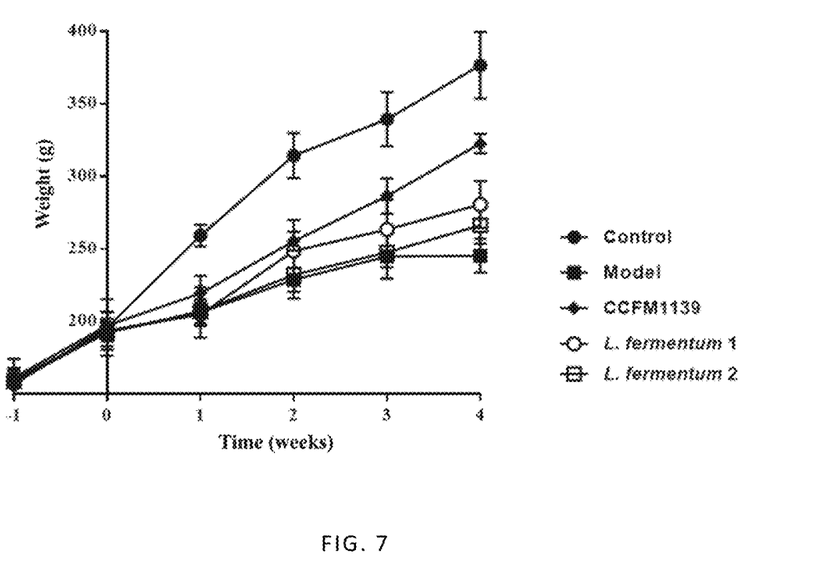
FIG. 7 shows graph of body weight change in rats.

From the results in FIG. 7, it can be found that the blank group with a normal diet showed a more significant trend of weight gain compared with the other groups. The average weight of the blank group was 376.64 g at week 4.

The weight of the model group began to stabilize at week 3, and at week 4, the average weight was 245.20 g.

The body weights of rats in the *L. fermentum* 1 and *L. fermentum* 2 groups reached 280.58 g and 266.17 g at week 4, respectively, and the body weights increased compared with the model group, but the effect was not as good as that in the *L. fermentum* CCFM1139 group.

The average weight of rats in the CCFM1139 group could reach 322.58 g at week 4, with the best effect in all experimental groups, and increased by about 80 g compared with the model group.

2. Effect of *L. fermentum* CCFM1139 on Pathogens of Periodontitis and *Lactobacillus* Colonization During the experiment, sterilized paper tips were inserted into periodontal pockets with sterilized forceps, in order to collect subgingival plaque from the left maxillary second molar of rats, placed for about 20 s and then taken out. The paper tips were inserted into EP tubes with 1 mL of sterile PBS, diluted and applied to the corresponding plates and counted as pathogen colonization test. The experiment was performed four times, at each week after the end of the molding respectively. The effect of different preventing and treating methods on colonization of pathogens in periodontitis was examined.

The solid plates used for colony counting were an MRS solid medium supplemented with vancomycin (20 µg/mL) and 20 g/L of agar for counting *Lactobacillus* in the rat oral cavity. A BHI solid medium supplemented with ampicillin (12 µg/mL), 5% (v/v) sheep blood and 20 g/L of agar and combined with colony morphological characteristics for counting single colonies of the *F. nucleatum* and *P. gingivalis* in the rat oral cavity.

Figure 8:
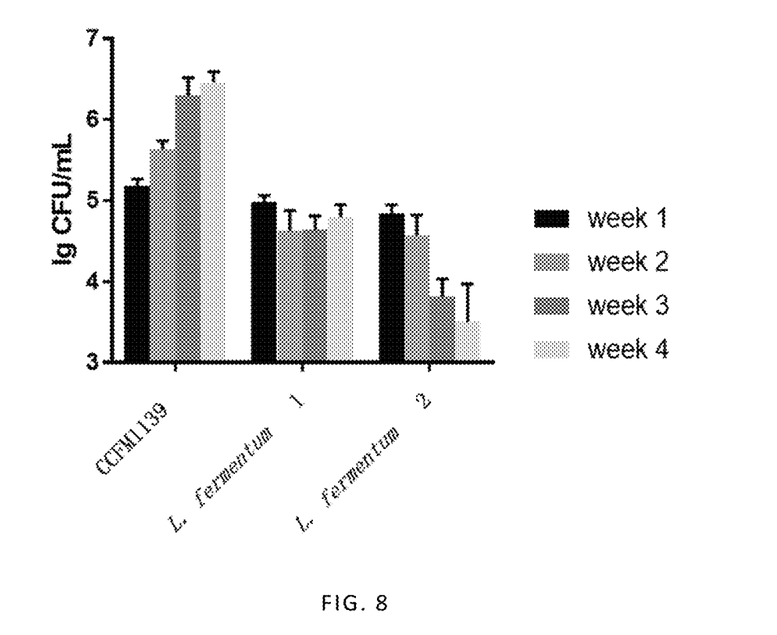
FIG. 8 shows colonization of *Lactobacillus* in the oral cavity of rats.

(1) According to the results of the *Lactobacillus* count in FIG. 8, colonization of the *L. fermentum* CCFM1139 in the CCFM1139 group was around $10^5$ CFU/mL at week 1, and colonization of the *Lactobacillus* exceeded $10^6$ CFU/mL at week 3 of the experiment.

In the *L. fermentum* 1 group, colonization of the *L. fermentum* 1 was about $10^5$ CFU/mL at week 1, gradually decreased at weeks 2-3, and was less than $10^5$ CFU/mL at week 4.

In the *L. fermentum* 2 group, colonization of the *L. fermentum* 2 gradually decreased over a period of 4 weeks, and was less than $10^4$ CFU/mL at week 4.

Therefore, the *L. fermentum* CCFM1139 has better oral colonization compared with *L. fermentum* 1 and *L. fermentum* 2.

Figure 9:
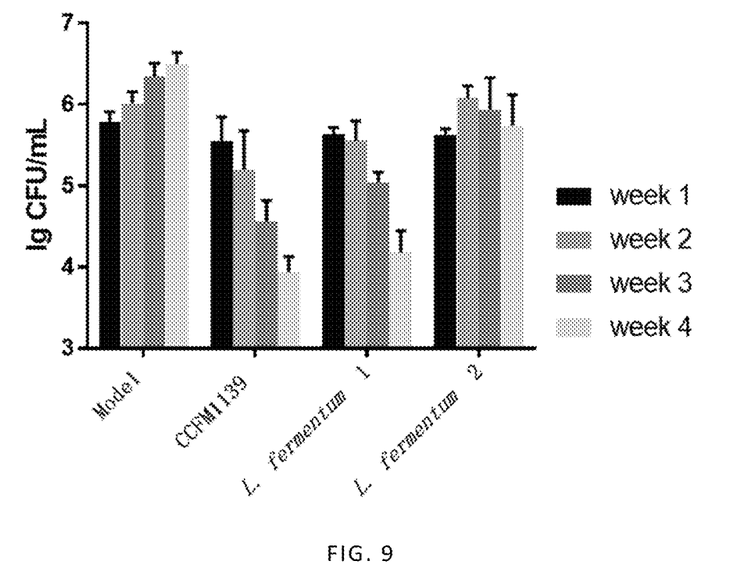
FIG. 9 shows colonization of the *P. gingivalis* in the oral cavity of rats.

(2) FIG. 9 shows colonization counts of the *P. gingivalis*. Colonization of the *P. gingivalis* could reach $1.5 \times 10^6$ CFU/mL in the Model group at week 4 of modelling. In 3 mediated groups, the *L. fermentum* CCFM1139 was the most effective, reducing colonization of the *P. gingivalis* to less than $10^4$ CFU/mL at week 4.

The *L. fermentum* 1 was the second most effective, with colonization of the *P. gingivalis* at slightly more than $10^4$ CFU/mL at week 4.

The *L. fermentum* 2 was the least effective, with colonization of the *P. gingivalis* consistently around $10^6$ CFU/mL over a mediated period of 4 weeks.

Figure 10:
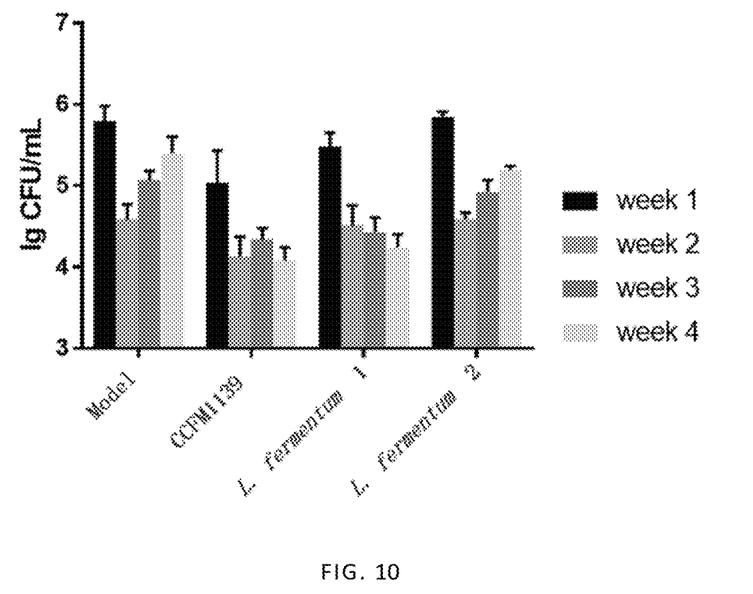
FIG. 10 shows colonization of the *F. nucleatum* in the oral cavity of rats.

(3) FIG. 10 shows colonization counts of the *F. nucleatum*. Colonization of the *F. nucleatum* in the Model group was about $1.5 \times 10^5$ CFU/mL at week 4. At week 4, colonization of the *F. nucleatum* in the CCFM1139 group and the *L. fermentum* 1 group was close to each other both with about $10^4$ CFU/mL. Colonization of the *F. nucleatum* in the CCFM1139 group was slightly less than that in the *L. fermentum* 1. The *L. fermentum* 2 had some inhibition effect on colonization of the *F. nucleatum*, but not as much as the CCFM1139 group and the *L. fermentum* 1 group. Colonization of the *F. nucleatum* reached $10^5$ CFU/mL at week 4.

In conclusion, the *L. fermentum* CCFM1139 has good oral colonization ability and has good inhibition effect on colonization of the periodontal pathogens *P. gingivalis* and *F. nucleatum* in the oral cavity.

3. Effect of *L. fermentum* CCFM1139 on Inflammatory Factors TNF-α and IL-8

0.1 g of rat gingival tissue was added to 0.9 mL of RIPA lysis solution containing phosphatase inhibitor and protease inhibitor for lysis, and then centrifuged at 12000 r/min for 10 min after being shattered by a tissue crusher. The precipitate was discarded and the supernatant was pipetted, and then the protein concentration was measured according to the instructions of a BCA protein concentration kit. At the same time, TNF-α and IL-8 in a rat gingival tissue in rat gingival tissues were measured according to the instructions of an ELISA kit for rat TNF-α and IL-8. The amount of inflammatory factors (TNF-α and IL-8)/total protein=relative expression of inflammatory factors (TNF-α and IL-8).

Figure 11:
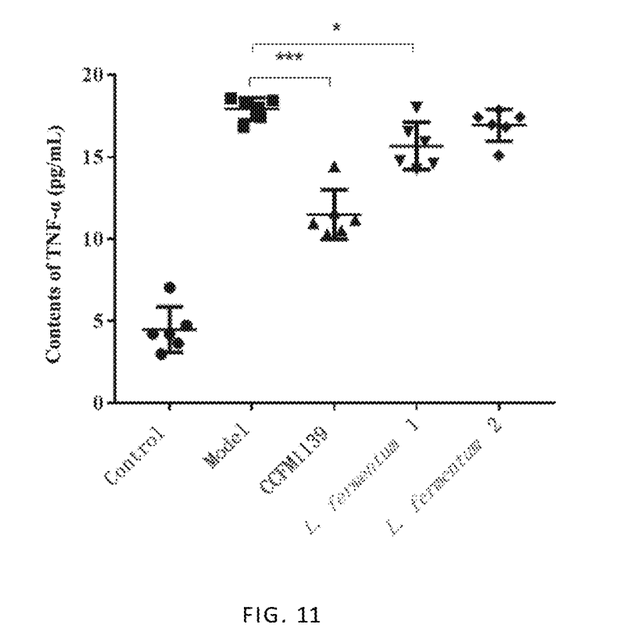
FIG. 11 shows relative expression of TNF-α in rat gingival tissues.
Figure 12:
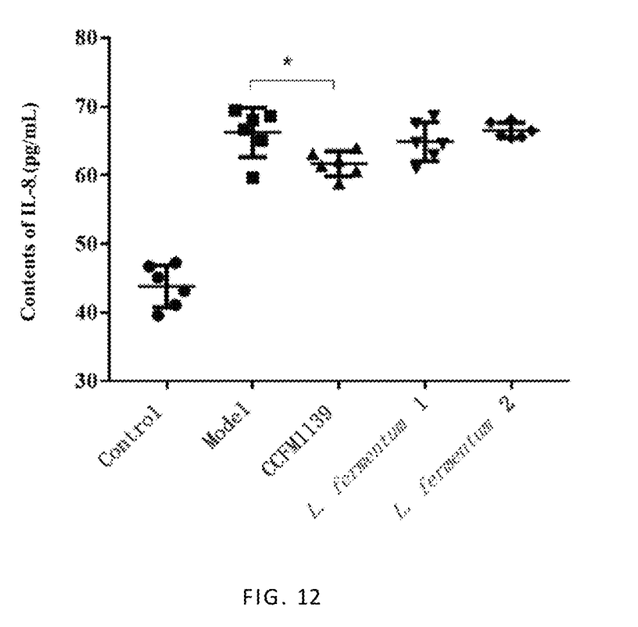
FIG. 12 shows relative expression of IL-8 in rat gingival tissues.

According to FIGS. 11-12, it can be seen that both inflammatory indexes, TNF-α and IL-8, appeared to be significantly upregulated in the gingival tissues of rats suffering from periodontitis relative to the blank group ($p<0.05$).

For the index of TNF-α, as shown in FIG. 11, both the *L. fermentum* CCFM1139 and the *L. fermentum* 1 could reduce the secretion of TNF-α to some extent, with the CCFM1139 having the best effect, and reducing the secretion of TNF-α from 18.015 pg/mg to 11.608 pg/mg.

For IL-8, as shown in FIG. 12, the *L. fermentum* 1 and the *L. fermentum* 2 did not significantly reduce the secretion of IL-8 (p>0.05), while the *L. fermentum* CCFM1139 could reduce the secretion of IL-8 from 66.674 pg/mg to 62.142 pg/mg.

4. Histological Observation

The rat maxillary bone tissues were trimmed and put into paraformaldehyde with a mass fraction of 4% for 48 h, placed in an EDTA solution with a mass fraction of 10%, decalcified at 4° C. for 7 days, dehydrated in alcohol step by step, routinely paraffin-embedded, longitudinally cut along the long axis of the tooth in the buccolingual direction (section thickness of 4 μm), and observed after HE staining.

Figure 13:
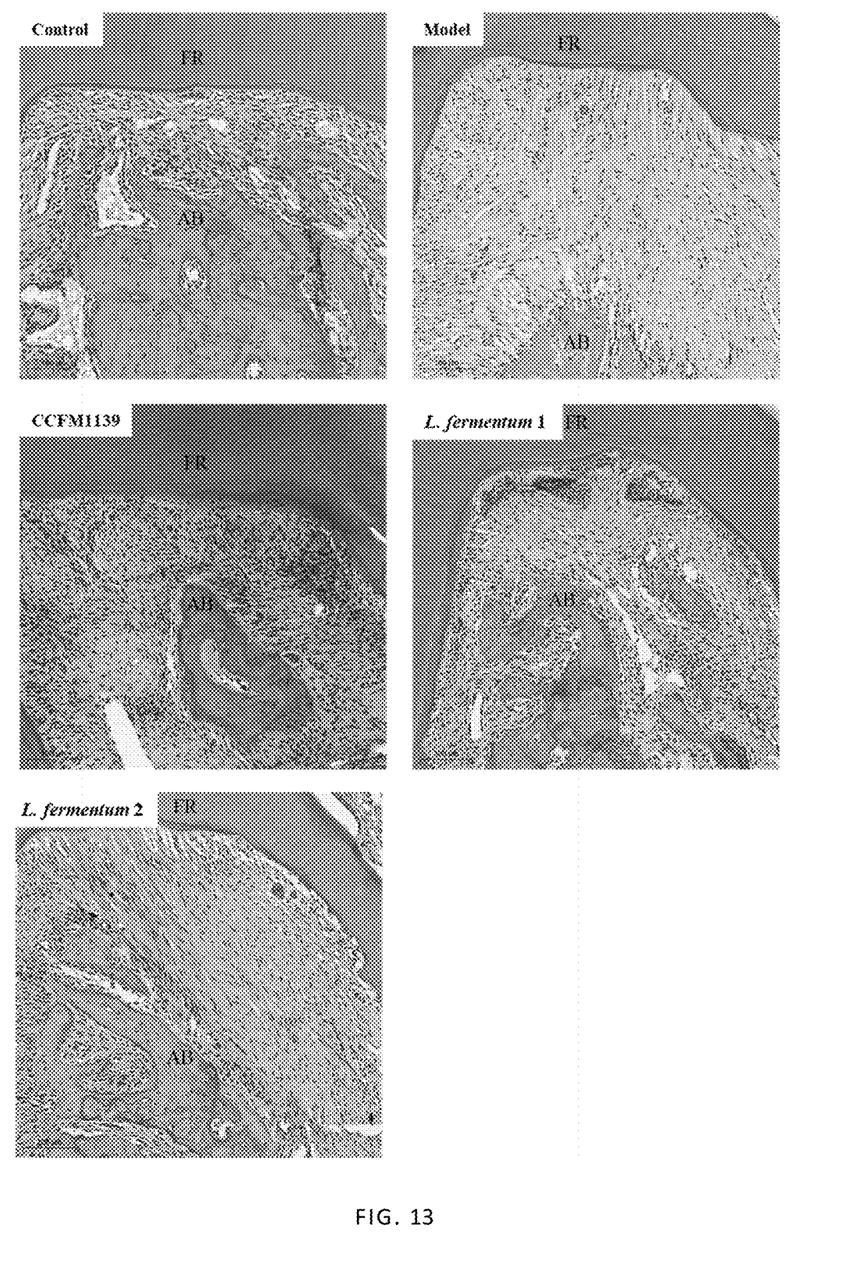
FIG. 13 shows pathological sections of rat periodontal tissues.

According to FIG. 13, alveolar bone of Control group rats was intact without resorption, and the height of the alveolar ridge crest was normal. The periodontal fibers were arranged neatly and densely. The alveolar bone resorption and periodontal fibers destruction were obvious in the Model group. There was no obvious resorption of rat alveolar bone tissues in the *L. fermentum* CCFM1139 group compared with the Model group. The periodontal fibroblasts were arranged neatly and not significantly separated from the cementum before. In the *L. fermentum* 1 group, although there was no disorder in arrangement of periodontal fibroblasts, the alveolar bone resorption was obvious and a small amount of inflammatory cell infiltration was seen. In contrast, in the *L. fermentum* 2 group, the alveolar ridge crest had an irregular morphology, and disorganized collagen fiber arrangement of periodontal tissues was seen.

5. Amount of the Alveolar Bone Resorption

Figure 14:
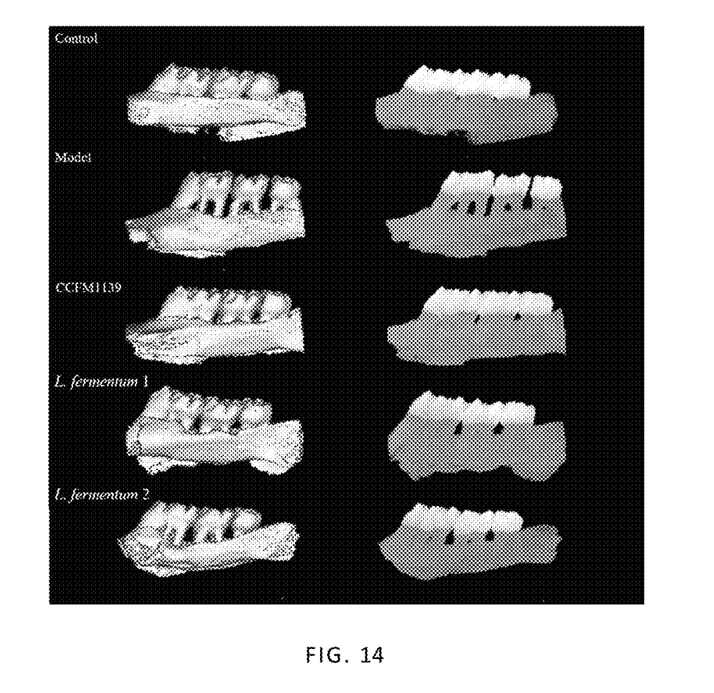
FIG. 14 shows Micro-CT map of rat maxillary teeth.

The maxillary bone of rats was fixed in paraformaldehyde with a mass fraction of 4% for 48 h. Soft tissues were removed, and the maxillary bone was washed and dried with clean water at the end. Maxillary bone samples were imaged by X-ray scanning with an in vivo Micro-CT imaging system. The parameters were voltage of 90 kV, current of 88 μA, field of view of 18 μm, acquisition time of 4 min, and camera mode of high resolution. A three-dimensional image of the maxilla was reconstructed by rotating each sample by 360°, as shown in FIG. 14. The alveolar bone resorption (ABL), i.e., the distance from cemento-enamel junction of the second molar to alveolar ridge crest, was measured at 4 sites per tooth, that is, proximal and distal ends at buccal and lingual sites. The average of the measured values at each site was the alveolar bone resorption value for the tooth, as shown in FIG. 15.

Figure 15:
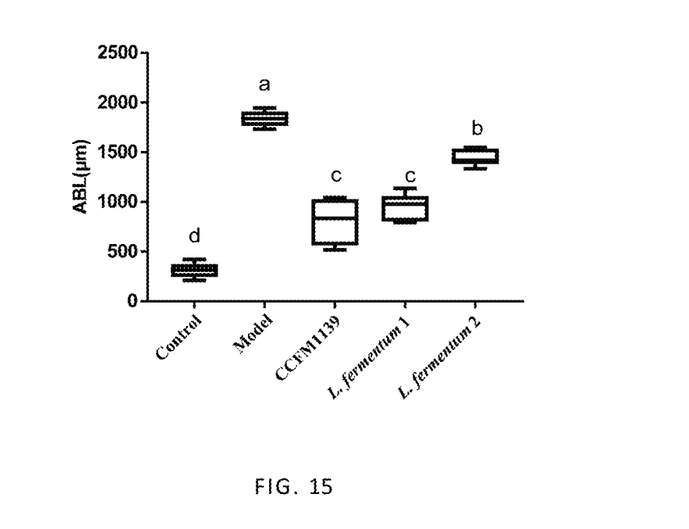
FIG. 15 shows the amount of the alveolar bone resorption in rats.

According to FIGS. 14-15, the alveolar bone in the Control group was smooth without obvious loss and the teeth were tightly aligned, and the amount of the alveolar bone resorption was 313.2 μm.

In the Model group, the alveolar bone resorption was obvious, the molar gap became larger, the alveolar bone showed a crater-like loss, the roots were exposed seriously, and the alveolar bone resorption amount reached 1838.0 μm.

The *L. fermentum* CCFM1139 group showed slight partial resorption of the alveolar bone, but the effect was better than that of the *L. fermentum* 1 and the *L. fermentum* 2 groups, with the alveolar bone resorption of 805.7 μm in the CCFM1139, while 994.3 μm and 1442.1 μm in the *L. fermentum* 1 and *L. fermentum* 2 groups, respectively. Thus, the *L. fermentum* CCFM1139 was effective in improving the alveolar bone resorption in rats with periodontitis.

Although the present disclosure has been provided as above in the preferred examples, it is not intended to limit the present disclosure. Any person skilled in the art can make various changes and modifications without departing from the spirit and scope of the present disclosure. Therefore, the protection scope of the present disclosure should be as defined in the claims

---

What is claimed is:

1. A product comprising: *Lactobacillus fermentum* (*L. fermentum*) CCFM1139, wherein the *L. fermentum* CCFM1139 was deposited in the Guangdong Microbial Culture Collection Center on Aug. 1, 2020, with the deposit number of GDMCC No: 61116; and
    wherein the product is a daily chemical product that is a mouthwash or toothpaste.

2. The product of claim 1, wherein the viable count of the *L. fermentum* CCFM1139 is not less than $1\times10^9$ CFU/mL or $1\times10^{12}$ CFU/g.

3. A product, comprising: *Lactobacillus fermentum* (*L. fermentum*) CCFM1139, wherein the *L. fermentum* CCFM1139 was deposited in the Guangdong Microbial Culture Collection Center on Aug. 1, 2020, with the deposit number of GDMCC No: 61116, wherein the product is a food, and wherein the food is a yogurt.

4. A method for preparing a product for treating periodontitis, comprising:
    providing an effective amount of *Lactobacillus fermentum* (*L. fermentum*) CCFM1139,
    adding to the product, the *L. fermentum* CCFM1139 which was deposited in the Guangdong Microbial Culture Collection Center on Aug. 1, 2020, with the deposit number of GDMCC No: 61116;
    wherein the product is a daily chemical product that is a mouthwash or toothpaste.

5. The method of claim 4, wherein the viable count of the *L. fermentum* CCFM1139 is not less than $1\times10^9$ CFU/mL or $1\times10^{12}$ CFU/g.

6. The product according to claim 3, wherein the viable count of the *L. fermentum* CCFM1139 is not less than $1\times10^9$ CFU/mL or $1\times10^{12}$ CFU/g.

* * * * *